United States Patent
Park et al.

(10) Patent No.: US 11,185,559 B2
(45) Date of Patent: Nov. 30, 2021

(54) TUMOR MICROENVIRONMENT-RESPONSIVE NANOCOMPLEX AND ANTICANCER COMPOSITION COMPRISING SAME

(71) Applicants: Korea National University of Transportation Industry-Academic Cooperation Foundation, Chungcheongbuk-do (KR); Industry Foundation of Chonnam National University, Gwangju (KR)

(72) Inventors: In Kyu Park, Gwangju (KR); Santhosh Kalash Rajendrakumar, Jeollanam-do (KR); Yong Kyu Lee, Chungcheongbuk-do (KR); Vishnu Revuri, Chungcheongbuk-do (KR)

(73) Assignees: Korea National University of Transportation Industry-Academic Cooperation Foundation, Chungcheongbuk-do (KR); Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 16/823,660

(22) Filed: Mar. 19, 2020

(65) Prior Publication Data

US 2020/0297759 A1    Sep. 24, 2020

(30) Foreign Application Priority Data

Mar. 20, 2019    (KR) .................. 10-2019-0031978

(51) Int. Cl.
| | | |
|---|---|---|
| *A61K 33/32* | (2006.01) | |
| *A61K 9/16* | (2006.01) | |
| *A61P 35/00* | (2006.01) | |
| *A61K 33/00* | (2006.01) | |
| *A61K 9/70* | (2006.01) | |

(52) U.S. Cl.
CPC ............ *A61K 33/32* (2013.01); *A61K 9/16* (2013.01); *A61K 9/7007* (2013.01); *A61K 33/00* (2013.01); *A61P 35/00* (2018.01)

(58) Field of Classification Search
CPC .......... A61P 29/00; A61P 19/02; A61P 25/00; A61P 25/28; A61P 27/06; A61P 3/10; A61P 43/00; A61P 1/00; A61P 11/00; A61P 15/10; A61P 17/00; A61P 17/06; A61P 25/22; A61P 3/04; A61P 31/18; A61P 35/00; A61P 9/04; A61P 13/12; A61P 25/04; A61P 25/06; A61P 25/16; A61P 27/02; A61P 27/12; A61P 29/02; A61P 3/00; A61P 3/08; A61P 31/04; A61P 31/06; A61P 37/02; A61P 5/50; A61P 9/10; A61K 31/44; A61K 31/535; A61K 2300/00; A61K 31/00; A61K 31/12; A61K 31/122; A61K 31/165; A61K 31/19; A61K 31/245; A61K 31/335; A61K 31/36; A61K 31/40; A61K 31/445; A61K 31/495; A61K 31/505; A61K 31/53; A61K 31/54; A61K 31/55; A61K 31/4545; A61K 45/06; A61K 47/00; A61K 33/32; A61K 9/16; A61K 9/7007

See application file for complete search history.

(56) References Cited

PUBLICATIONS

Revuri et al. White-Light-Emitting Carbon Nano-Onions: A Tunable Multichannel Fluorescent Nanoprobe for Glutathione-Responsive Bioimaging ACS Appl. Nano Mater. 2018, 1, 2, 662-674 Publication Date: Dec. 26, 2017 https://doi.org/10.1021/acsanm.7b00143 Copyright © 2017 American Chemical Society). (Year: 2017).*

Revuri, V. et al. "White-Light-Emitting Carbon Nano-Onions: A Tunable Multichannel Fluorescent Nanoprobe for Glutathione-Responsive Bioimaging" ACS Appl. Nano Mater. 2018, 1, 662-674 (Year: 2018).*

\* cited by examiner

*Primary Examiner* — Andrew S Rosenthal
(74) *Attorney, Agent, or Firm* — RatnerPrestia (57) ABSTRACT

Various embodiments of the present disclosure are to provide a tumor microenvironment-responsive nanocomplex capable of presenting a novel paradigm for tumor therapy by reprogramming tumor microenvironments and an anticancer composition containing the same.

**3 Claims, 8 Drawing Sheets
(8 of 8 Drawing Sheet(s) Filed in Color)**

TUMOR MICROENVIRONMENT-RESPONSIVE NANOCOMPLEX AND ANTICANCER COMPOSITION COMPRISING SAME

CROSS REFERENCE TO RELATED APPLICATION

This application claims priority to Korean Patent Application No. 10-2019-0031978, filed Mar. 20, 2019, the contents of such application being incorporated by reference herein.

BACKGROUND OF THE INVENTION

1. Field of the Invention

The present disclosure relates to a tumor microenvironment-responsive nanocomplex and an anticancer composition containing the same.

2. Description of the Prior Art

Although cancer is one of the leading causes of morbidity worldwide, most anticancer therapies still rely on conventional radiotherapy, chemotherapy, and other surgery-mediated techniques to treat tumor malignancies. Cancer cells have an abnormal metabolism compared with normal cells, thereby creating a microenvironment conducive for tumor formation and progression. Cancer cells evolve in the tumor microenvironment (TME) by communicating with adjacent stromal cells and orchestrating cellular and molecular events in the surrounding tissue to promote survival, growth, and metastasis thereof. Understanding the importance of the TME can lead to a development of efficient therapeutic technologies that can not only kill cancer cells but also damage or reprogram the TME.

Tumor hypoxia is an in-vitro oxygen stress created around most solid tumors, resulting from distorted tumor vasculatures surrounding hyperproliferative cancer cells. Studies suggest that hypoxic environments not only impart cancer cells with chemotherapeutic multidrug resistance, resulting from the poor penetration of chemotherapeutic drugs in avascular hypoxic solid tumors, but also promote the secretion of multidrug-resistant permeability glycoprotein (P-GP1) transporter proteins in cancer cells. It was furthermore found that the depleted oxygen levels due to hypoxic cancer cells result in up to 3-fold reduction in the efficacies of radio-sensitization and radiation-based therapeutics.

Recently, many studies have been conducted targeting tumor hypoxia as a potential anti-tumor therapy.

SUMMARY OF THE INVENTION

An aspect of the present disclosure is to provide a tumor microenvironment-responsive nanocomplex capable of presenting a novel paradigm for tumor therapy by reprogramming tumor microenvironments and an anticancer composition containing the same.

In accordance with an aspect of the present disclosure, there is provided a tumor microenvironment-responsive nanocomplex. The tumor microenvironment-responsive nanocomplex may include: a manganese dioxide ($MnO_2$) sheet; and carbon nano-onions (CNOs) embedded in the manganese dioxide sheet.

In accordance with another aspect of the present disclosure, there is provided an anticancer composition. The anticancer composition may include the nanocomplex.

According to the present disclosure, the tumor microenvironment-responsive nanocomplexes of the present disclosure have a biologically stable structure with non-toxicity and can modulate the disproportion of hydrogen peroxide secreted excessively by cancer cells in the hypoxic tumor microenvironments. That is, the tumor microenvironment-responsive nanocomplexes can transmute the hypoxic tumor microenvironment into normoxia through oxygen supply. In addition, the tumor microenvironment-responsive nanocomplexes can suppress cancer cell proliferation by inhibiting hypoxia-inducible factor (HIF1-α).

Furthermore, the nanocomplexes of the present disclosure can maximize image-guided photothermal therapeutic efficacy. The nanocomplexes of the present disclosure produce oxygen through catalase-mimicking activity when exposed to hydrogen peroxide in the tumor-microenvironments, thereby inhibiting tumor adaptation to hypoxia, leading to the sensitization of tumor cells to photothermal therapy (PTT). Accordingly, the nanocomplexes of the present disclosure in combination with PTT can mitigate the tumor-associated hypoxia, thereby potentiating therapeutic efficacy. That is, tumor recurrence and metastasis can be inhibited through the therapy using the nanocomplexes of the present disclosure.

BRIEF DESCRIPTION OF THE DRAWINGS

The patent or patent application file contains drawings executed in color. Copies of this patent or patent application publication with color drawings will be provided by the Office upon request and payment of the necessary fee.

The above and other aspects, features and advantages of the present disclosure will be more apparent from the following detailed description taken in conjunction with the accompanying drawings.

DETAILED DESCRIPTION OF THE EXEMPLARY EMBODIMENTS

Hereinafter, various embodiments of the present disclosure are described. It should be understood that embodiments and terminologies used herein are not intended to limit the technology described in the present disclosure to particular forms of embodiments, but to cover various modifications, equivalents, and/or alternatives of corresponding embodiments.

Figure 1:
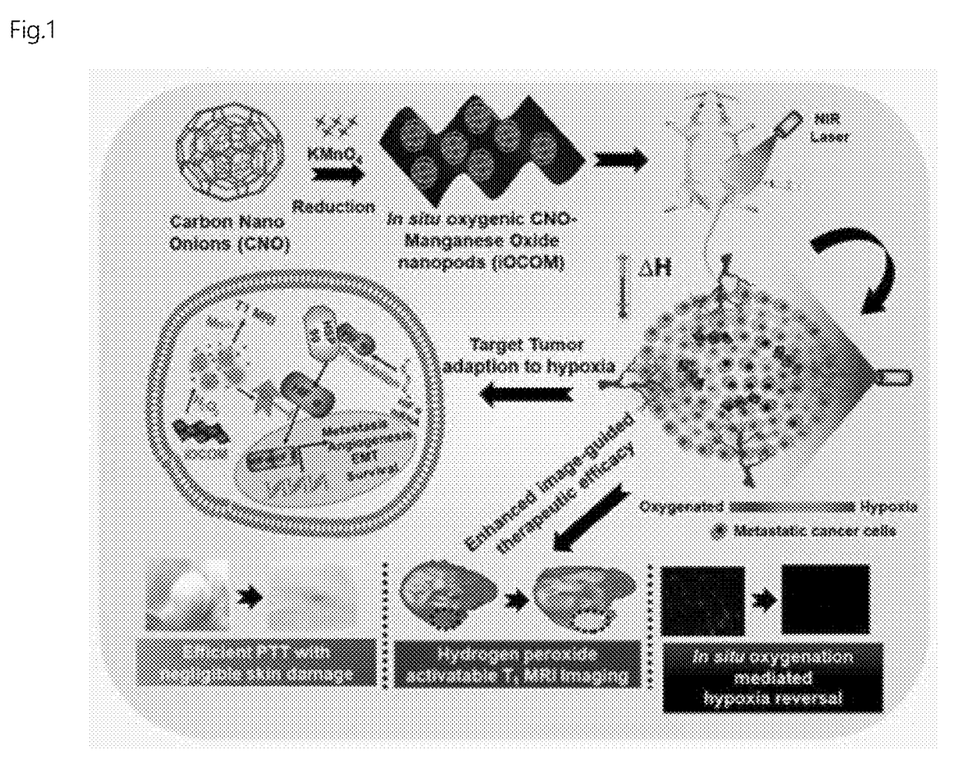
FIG. 1 is a schematic diagram showing the use of carbon nano-onions (CNOs) and in situ oxygenic CNO-manganese oxide nanopods (iOCOMs) to reprogram the tumor microenvironment (TME) and produce efficient photothermal therapy (PTT).
Figure 2:
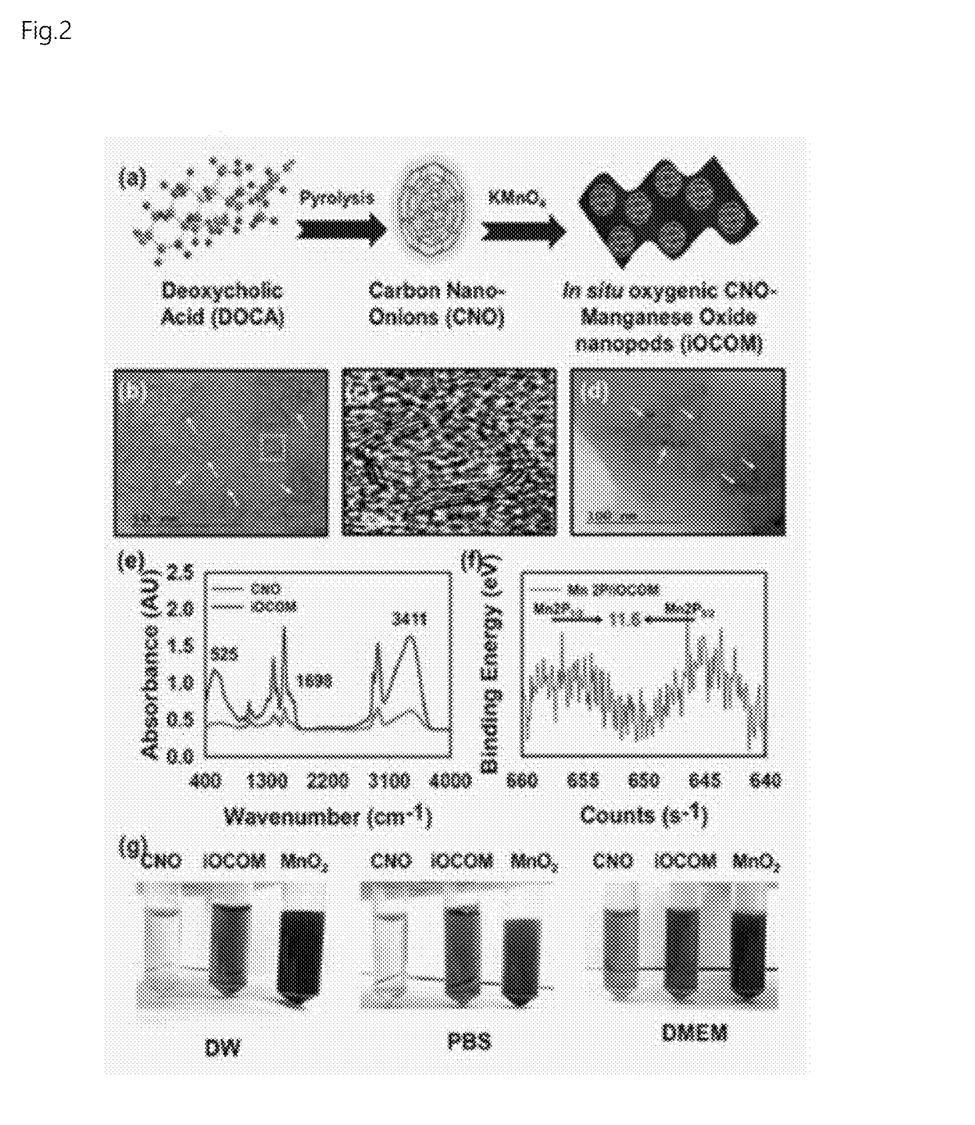
FIG. 2A is a schematic diagram showing CNOs synthesized from the pyrolysis of DOCA and the synthesis of iOCOMs ($KMnO_4$ reduction).
FIG. 2B is a field-emission transmission electron microcopy (FE-TEM) image of CNOs (indicated by arrows).
FIG. 2C shows a multiple fullerene structure of CNOs in a part indicated by a box in FIG. 2B.
FIG. 2D is a FE-TEM image of iOCOMs.
FIG. 2E is ATR-FTIR spectra of CNOs and iOCOMs.
FIG. 2F is high-resolution XPS manganese spectra of iOCOMs.
FIG. 2G shows the investigation results of stabilities of CNOs, iOCOMs, and $MnO_2$ in distilled water (DW), PBS, and DMEM media.

Referring to FIG. 1, tumor microenvironment-responsive nanocomplexes (in situ oxygenic carbon nano-onion/manganese oxide nanopods, iOCOMs) according to various embodiments of the present disclosure may include: manganese dioxide ($MnO_2$) sheets; and carbon nano-onions (CNOs) embedded in the manganese dioxide sheets. Referring to FIG. 2A, Carbon nano-onions (CNOs) may be synthesized through pyrolysis of deoxycholic acid (DOCA). The nanocomplexes (iOCOMs) of the present disclosure may be synthesized by reducing potassium permanganate ($KMnO_4$) to $MnO_2$ nanopods in the presence of CNOs.

The tumor microenvironment-responsive nanocomplexes of the present disclosure have a biologically stable structure and are nontoxic, and can modulate the disproportion of hydrogen peroxide secreted excessively by cancer cells in the hypoxic tumor microenvironments. That is, the tumor microenvironment-responsive nanocomplexes can transmute the hypoxic tumor microenvironment into normoxia through oxygen supply. In addition, the tumor microenvironment-responsive nanocomplexes can suppress cancer cell proliferation by inhibiting hypoxia-inducible factor (HIF1-α).

Furthermore, the nanocomplexes of the present disclosure can maximize image-guided photothermal therapeutic efficacy. The nanocomplexes of the present disclosure produce oxygen through catalase-mimicking activity when exposed to hydrogen peroxide in the tumor-microenvironments, thereby inhibiting tumor adaptation to hypoxia, leading to the sensitization of tumor cells to photothermal therapy (PTT). Accordingly, the nanocomplex of the present disclosure in combination with PTT can mitigate the tumor-associated hypoxia, thereby potentiating therapeutic efficacy. That is, tumor recurrence and metastasis can be inhibited through the therapy using the nanocomplexes of the present disclosure.

The anticancer compositions according to various embodiments of the present disclosure can contain the above-described nanocomplexes.

Hereinafter, the present disclosure will be described in detail with reference to examples and test examples.

However, the following examples and test examples are merely for illustrating the present disclosure, and the present disclosure is not limited by the following examples and test examples.

Example—Synthesis of iOCOMs

CNOs were synthesized using sodium deoxycholate (DOCA) as a precursor by a pyrolysis method. Briefly, 500 mg of DOCA was added to a 50-mL beaker, placed in a heating mantle, and then heated at 400° C. for 90 min. As the temperature increased, the color of DOCA changed from white to dark brown, indicating the synthesis of CNOs. Later, 40 mL of double-distilled water ($ddH_2O$) was added to the above sample, followed by sonication at room temperature for 30 min. The obtained dark brown solution was dialyzed using a dialysis membrane (molecular weight cut-off, MWCO, 1 kD) for 2 days by replacing dialysis media ($ddH_2O$) every 6 h. The dialyzed samples were freeze-dried.

The synthesis of iOCOMs was carried out by adding 100 μL of $KMnO_4$ (2 mg/mL) to 2 mL of CNOs (2.5 mg/mL) to reduce $KMnO_4$ to $MnO_2$. The samples were incubated for 10 min.

As described in the above example, CNOs can be synthesized using natural bile acid, deoxycholic acid (DOCA) following the pyrolysis method. DOCA is a naturally produced secondary bile acid that is secreted from the bile in the liver. These biomolecules are relatively economical and nontoxic in the biological system.

DOCA has a tetracyclic steroidal ring structure with the distribution of hydroxyl and carboxyl groups throughout the hydrophobic steroidal rings. During the pyrolysis, the dealkylation, dehydrogenation, and dehydrogenation of DOCA (nucleation) facilitate the conversion of steroidal structures into aromatic structures and aid the growth of the graphene core structures. However, the exact mechanism for the formation of multiple-layer rings has not yet been discovered.

Test Example 1—Characterization of CNOs and iOCOMs

Referring to FIG. 2B, the presence of multiple fullerene-like structures with six to eight concentric onion rings were confirmed in CNOs. Referring to FIG. 2C, the interplanar d lattice spacing of the synthesize CNOs was 0.34 nm, which was similar to that for previously reported CNOs.

The surface coating of CNOs with manganese dioxide accelerated TEM-responsive T1 MRI imaging as well as peroxide quenching. iOCOMs were synthesized by reducing potassium permanganate ($KMnO_4$) to $MnO_2$ nanopods in the presence of CNOs. As shown in FIG. 2D, CNOs were embedded in the $MnO_2$ sheets.

Referring to FIG. 2E, FT-IR spectra confirmed the presence of iOCOMs through a new peak at 525 $cm^{-1}$. In addition, the shift in the peak at 1698 $cm^{-1}$ indicated that the carboxyl groups of CNOs were involved in the reduction of $KMnO_4$ to $MnO_2$ as well as the binding of CNOs on the $MnO_2$ sheets.

Referring to FIG. 2F, high-resolution XPS spectra confirmed the presence of $MnO_2$ in iOCOMs. FIG. 2G shows the stabilities of CNOs and iOCOMs in different biological media. iOCOMs improved biological stability in distilled water, PBS, and DMEM compared with $MnO_2$, indicating that CNOs not only reduced $KMnO_4$ to $MnO_2$ but also improved stability in biological media.

Test Example 2—Oxygenic Activity Evaluation

Figure 3:
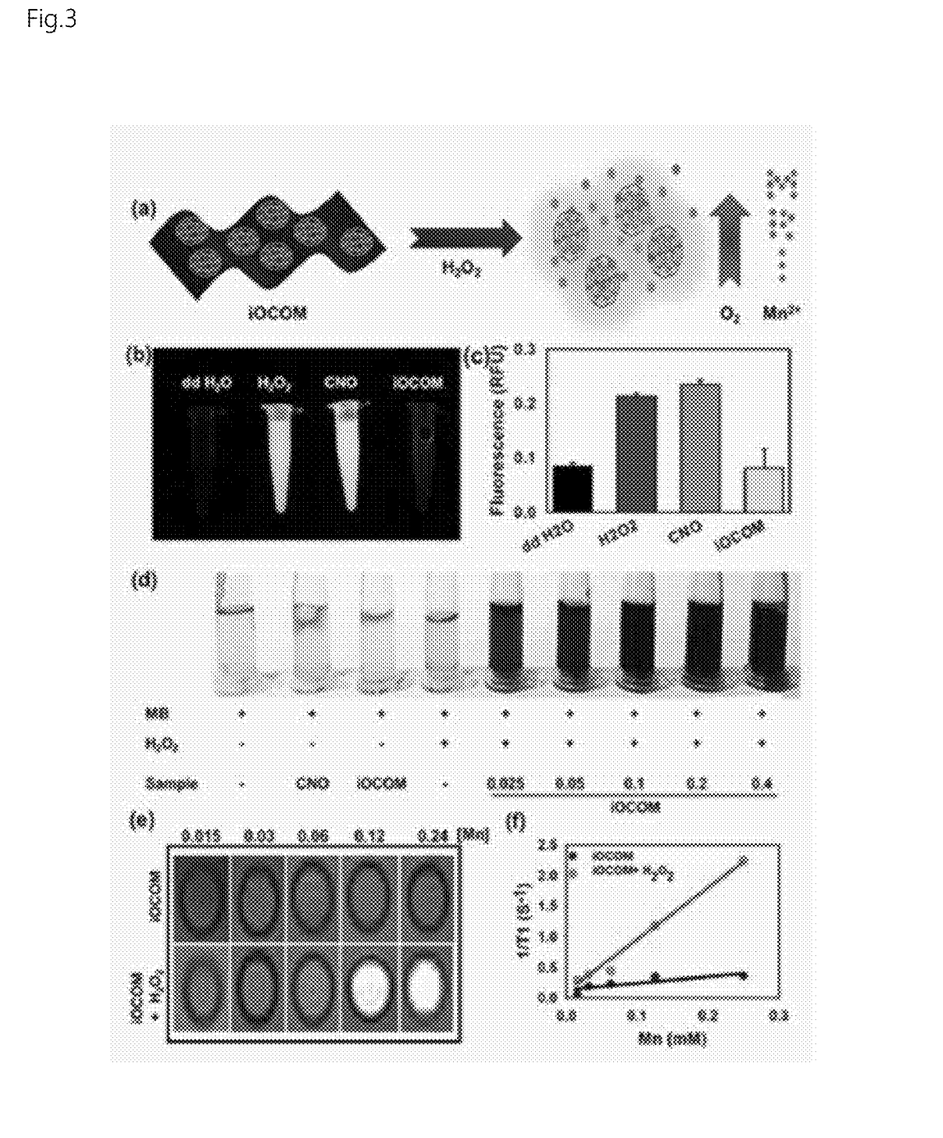
FIG. 3A is a schematic diagram depicting the release of Mn2+ ions as well as the increase in the oxygen concentration from iOCOMs in the presence of hydrogen peroxide ($H_2O_2$).
FIG. 3B shows evaluation results of $H_2O_2$ quenching by iOCOM OxiVision Green, a $H_2O_2$-sensitive fluorescent probe.
FIG. 3C shows the measurement results of relative fluorescence unit (RFU) of OxiVision Green in the presence of $H_2O_2$, CNOs, and iOCOMs.
FIG. 3D shows blue bottle experiment results by methylene blue indicating oxygen production in the $H_2O_2$-treated iOCOM samples.
FIG. 3E shows the results of T1 MRI spectra of iOCOMs in the presence of $H_2O_2$.
FIG. 3F shows the results of concentration-dependent relaxation rates of iOCOMs in the presence and absence of $H_2O_2$.

Referring to FIG. 3A, during the degradation of $H_2O_2$, a $MnO_2$-based nanomaterial assists in the production of oxygen. The following Expression (1) shows an interaction mechanism between $MnO_2$ and $H_2O_2$.

$$MnO_2 + H_2O_2 \rightarrow Mn^{2+} + 2H_2O + O_2 \quad \text{Expression (1)}$$

Therefore, OxiVision Green as a $H_2O_2$-responsive fluorescence nanoprobe was used to investigate the $H_2O_2$ quenching capabilities of iOCOMs. As shown in FIG. 3B, both CNOs and $H_2O_2$ showed similar fluorescence intensities, indicating that CNOs alone could not quench $H_2O_2$. However, referring to FIG. 3C, the addition of iOCOMs to the $H_2O_2$ solution resulted in a marked reduction in fluorescence intensity, which was similar to those of samples treated with distilled water ($ddH_2O$). These results confirmed that iOCOMs can effectively quench $H_2O_2$ in the biology system.

To further evaluate in situ oxygenation of iOCOMs, a blue bottle experiment using methylene blue (MB) was carried out. The increased blue intensity means that oxygen production of the solution increased. MB acts as a mediator in accelerating the oxidation of glucose by reducing itself to leucomethylene blue (LB). As shown in FIG. 3D, the MB solution treated with CNOs, iOCOMs, or $H_2O_2$ alone turned colorless due to the reduction of MB to LB. Interestingly, the MB solution treated with both iOCOMs and $H_2O_2$ retained the blue color from MB. The release of dissolved oxygen during the iOCOM-assisted dismutation of $H_2O_2$, preventing the reduction of MB. In addition, the intensity of the blue color from MB was reduced when the concentration of iOCOMs was reduced in the solution. These results confirmed the oxygenic activity of iOCOMs.

Then, $H_2O_2$ responsive T1 MRI imaging of iOCOMs was observed. As shown in FIG. 3E, iOCOMs have T1 MRI contrast imaging only in the presence of H2OD. Referring to FIG. 3F, the relaxation rate showed a linear profile under sequential concentration gradients of iOCOMs in the presence of $H_2O_2$.

Test Example 3—Thermal Characteristics Assay

Figure 4:
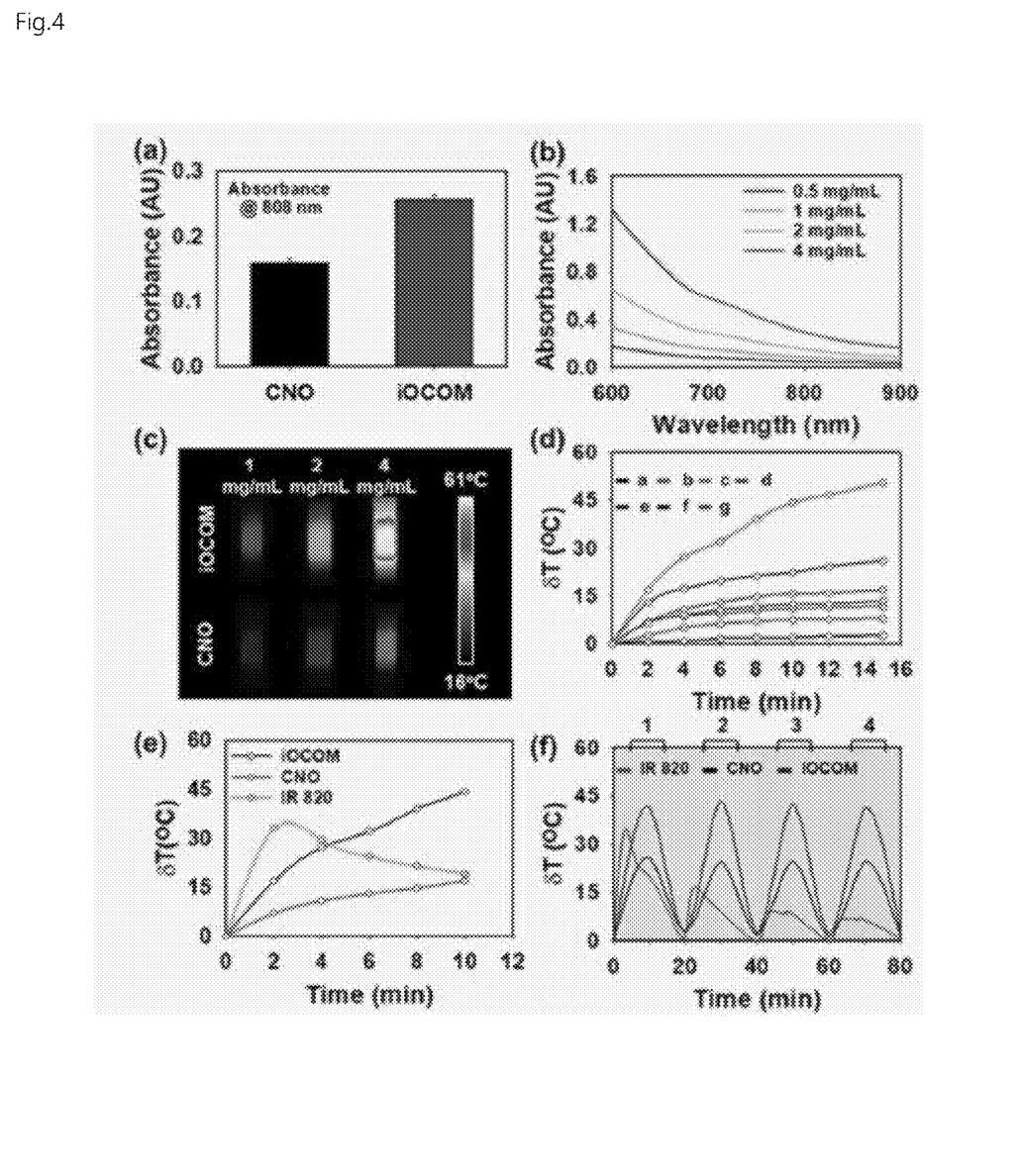
FIG. 4A shows the measurement results of absorbance units (AU) of CNOs (1 mg/mL) and iOCOMs (1 mg/mL) at 808 nm.
FIG. 4B shows the results of concentration-dependent absorbance spectra of iOCOMs.
FIG. 4C shows thermal images showing heat generation from CNOs and iOCOMs after irradiation with an NIR laser (808 nm; 2 W/cm² for 15 min).
FIG. 4D is a graph of concentration-dependent heat generation from CNOs and iOCOMs after irradiation with an NIR laser (808 nm; 2 W/cm²). (a: dd $H_2O$ (2 mg/mL), b: CNO (1 mg/mL), c: CNO (2 mg/mL), d: CNO (4 mg/mL), e: iOCOM (1 mg/mL), f: iOCOM (2 mg/mL), g: iOCOM (4 mg/mL)).
FIG. 4E shows the comparison results of heat profiles among IR 820, CNOs, and iOCOMs.
FIG. 4F shows the comparison results of recycling heating profiles among IR 820, CNOs, and iOCOMs under NIR irradiation (808 nm; 2 W/cm²).

For near-infrared laser-mediated photothermal therapy (PTT), a material should not only possess sufficient energy absorption in the near-infrared (NIR) regions but also emit the absorbed energy in the form of heat. Interestingly, both CNOs and iOCOMs have absorbance in the NIR regions while investigating photoluminescence characteristics. Although both nanomaterials exhibited NIR absorbance, referring to FIG. 4A, the absorbance values of CNOs at the NIR wavelength of 808 nm were lower than those of iOCOMs. As shown in FIG. 4B, iOCOMs showed a concentration-dependent reduction in the absorbance values in the near-infrared ray regions (700-900 nm). Since CNOs and iOCOMs showed absorbance in the near-infrared regions, it can be assumed that the nanomaterials according to the example can release the absorbed energy in the form of heat and can function as a potent PTT sensitizer under near-infrared laser irradiation. Therefore, the concentration-dependent heat generation from CNOs and iOCOMs under near-infrared irradiation was tested. Referring to FIG. 4C, both CNOs and iOCOMs can be used as near-infrared thermal imaging agents when irradiated with an NIR laser (excitation wavelength 808 nm; time of exposure: 10 min). Referring to FIG. 4D, the degree of heat generation, δT value, for iOCOM was almost 34° C., which was more efficient than that for CNOs (δT value: 15° C.). The heat generation from CNOs and iOCOMs was compared with that from IR 820, a conventional NIR PTT agent. Referring to FIG. 4E, iOCOMs showed homogeneous heating profiles compared with those for IR 820. Although IR 820 requires a minimal time to achieve enhanced thermal signs, referring to FIG. 4F, the repetitive heat generation cycle test showed a reduction in heat production from IR 820 after the second cycle of laser irradiation. This could be due to the degradation of organic dyes after NIR irradiation. However, CNOs and iOCOMs showed consistent thermal characteristics even after four cycles of laser irradiation. These results confirmed that CNOs and iOCOMs can be used as efficient photothermal sensitizers for PTT.

Test Example 4—Hypoxic Condition Analysis and In-Vitro Test of Apoptosis by NIR Laser Irradiation Complex III of the electron transport chain in mitochondria facilitates the secretion of $H_2O_2$ in cancer cells under hypoxic conditions. To investigate that iOCOMs produce oxygen in the presence of $H_2O_2$ and mitigate the hypoxic levels in cancer cells, an in-vitro hypoxic model was created by treating KB cells with $CoCl_2$ for 24 h. Peroxy orange 1 (PO1), a $H_2O_2$-sensitive probe, was used to stain the hypoxic areas in cancer cells.

Figure 5:
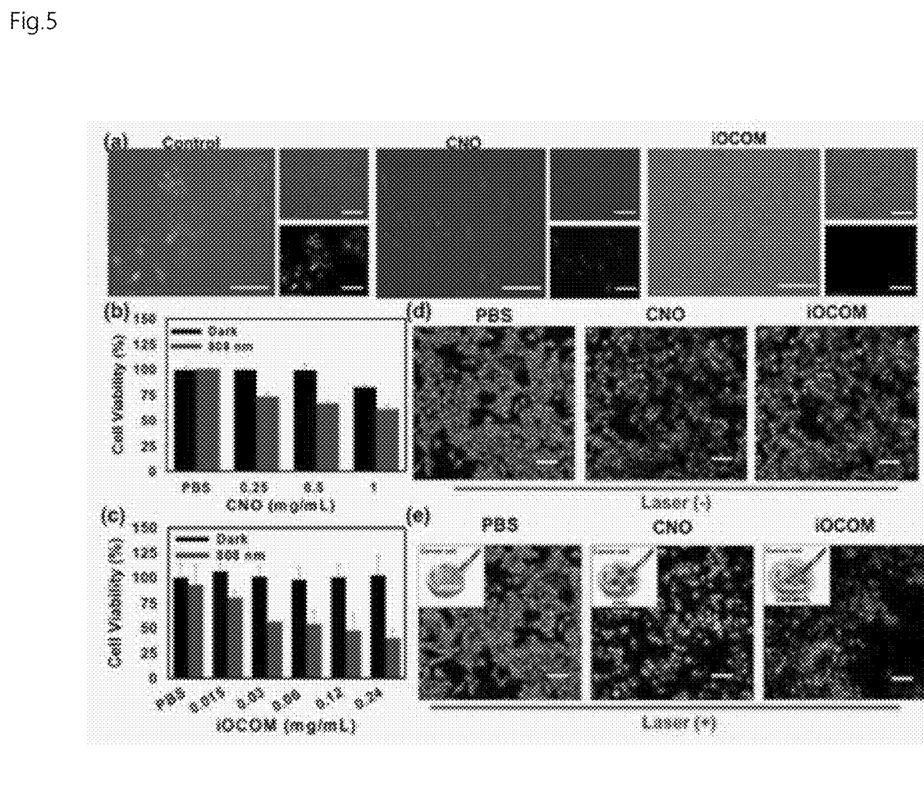
FIG. 5A shows the analysis results of hypoxia conditions in cancer cells.
FIG. 5B shows the MTT analysis results showing the concentration-dependent apoptosis when the cells were treated with CNOs and irradiated with an NIR laser.
FIG. 5C shows the MTT analysis results showing the concentration-dependent apoptosis when the cells were treated with iOCOMs and irradiated with an NIR laser.
FIGS. 5D and 5E show the analysis results of apoptotic profiles before and after NIR laser irradiation.

As shown in FIG. 5A, saline treated or CNO-treated KB cells showed enhanced PO1 fluorescence, confirming that the secretion of $H_2O_2$ was enhanced in cancer cells under hypoxic conditions. The KB cells treated with iOCOMs showed a strong reduction in PO1 fluorescence, confirming that iOCOMs reduced the $H_2O_2$ levels and thereby mitigated the hypoxic conditions in cancer cells. The reduced PO1 intensity in the KB cells treated with iOCOMs was similar to that in the control normoxic KB cells. These results confirmed that iOCOMs can modulate the hypoxic cancer environment into normoxia.

The NIR PTT activities of both CNOs and iOCOMs were investigated by incubating cells with different concentrations of CNOs and iOCOMs, followed by irradiating the cells with an NIR laser (excitation wavelength 808 nm) for 3 min. As shown in FIG. 5B, at low concentrations, at least 50% of the cells died by CNO treatment, whereas as shown in FIG. 5C, 40% of the cells died by iOCOM treatment.

Live and dead assays were used to qualitatively determine the PTT activities. Referring to FIG. 5D, the CNO- and iOCOM-treated groups showed little apoptosis before NIR laser irradiation. However, referring to FIG. 5E, an increase in the dead cell profiles in iOCOM-treated cells compared to that in the CNO group was observed when the cells were irradiated with the NIR laser (808 nm, 2 W/cm$^2$) for 3 min. These results suggest that CNOs and iOCOMs can be an effective nanomaterial for PTT.

Test Example 5—T1 MRI Imaging and In-Vivo Test of Thermal Imaging Measurement

Figure 6:
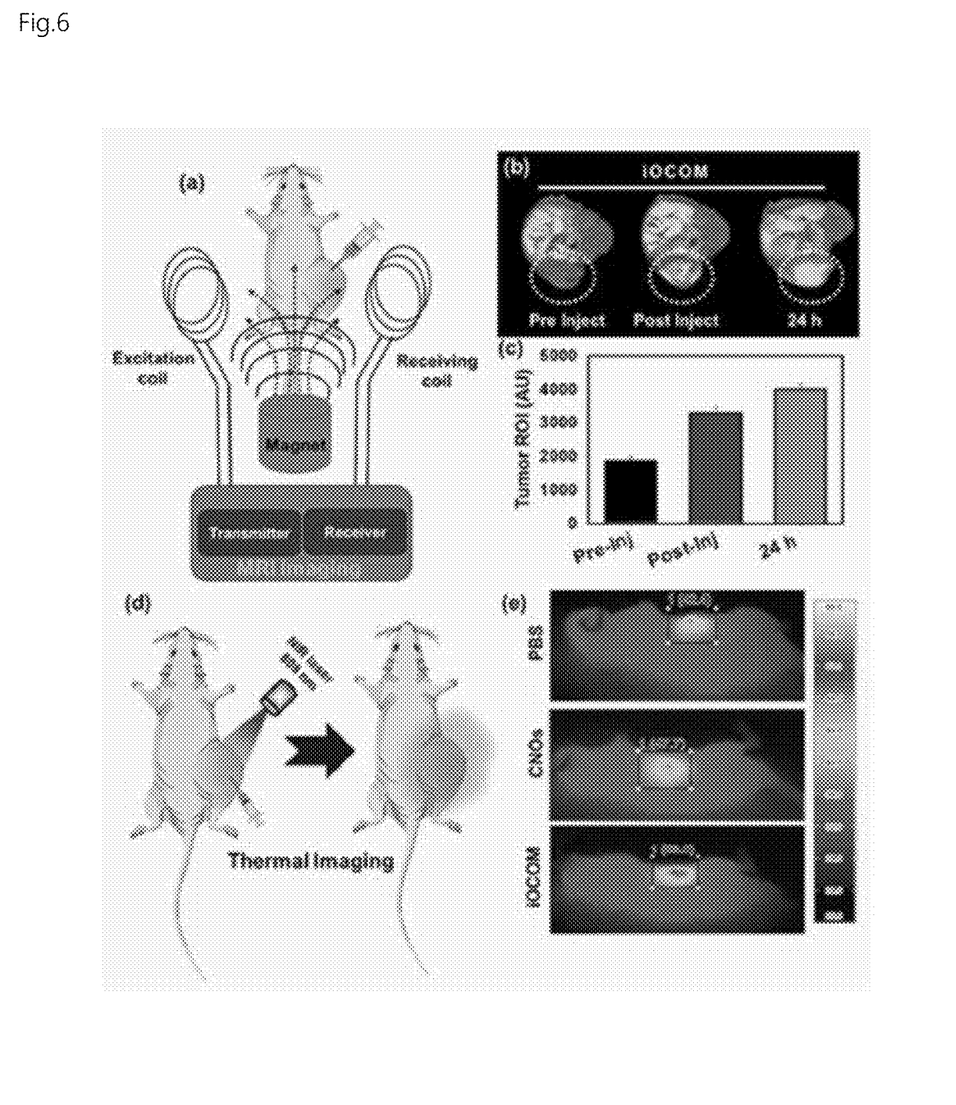
FIG. 6A is a schematic diagram related with T1 MRI imaging in KB tumor xenograft mice after iOCOM injection.
FIG. 6B shows T1 MRI imaging from the iOCOM-injected KB tumor xenograft after different time points.
FIG. 6C shows T1 MRI signal intensities of iOCOMs at different time points.
FIG. 6D is a schematic diagram related with thermal imaging from tumor xenograft-embedded nude mice after iOCOM injection.
FIG. 6E shows thermal imaging depicting the heat generation at the tumor site after CNOs and iOCOM injected mice were irradiated with an NIR laser for 15 min.

The in-vivo test of iOCOMs was carried out by developing a KB cell xenograft model in Balb/C nude mice. Referring to FIG. 6A, intratumoral (IT) injections of iOCOMs were administered to the tumor-bearing mice to investigate the T1 MRI imaging of the nanomaterial. As shown in FIG. 6B, the T1 MRI contrast imaging indicated the time-dependent homogenous distribution of iOCOMs. As shown in FIG. 6C, the average T1 MRI signal intensity at the tumor site increased 24 h after administration. The reason for this significant enhancement in T1 MRI contrast was that the rate of degradation of $MnO_2$ into $Mn^{2+}$ ions from iOCOMs in the localized $H_2O_2$ environment was higher after 24 h compared with that immediate post injection. This suggests that a hypoxic environment is necessary to generate significant T1 MRI contrast and hypoxia-responsive T1 MRI imaging from the iOCOM nanomaterials. These results confirmed the retention of the nanomaterial at the tumor site for 24 h.

Referring to FIG. 6D, an infrared thermal imaging camera was used to record the heat generated from the CNO- and iOCOM-injected mice after NIR laser irradiation (excitation wavelength: 808 nm, power: 2 W/cm$^2$) for 15 min. The thermal imaging shown in FIG. 6E shows that the iOCOM-treated animals showed the enhanced heat generation compared with CNO-treated animals. The animals treated with iOCOMs generated a maximum heat level of 53° C., which was 6° C. higher than that in the animals treated with CNOs. This heat generation from iOCOMs is sufficient to cause irreversible damage to DNA, denature proteins, and ensure no tumor recurrence after PTT.

Figure 7:
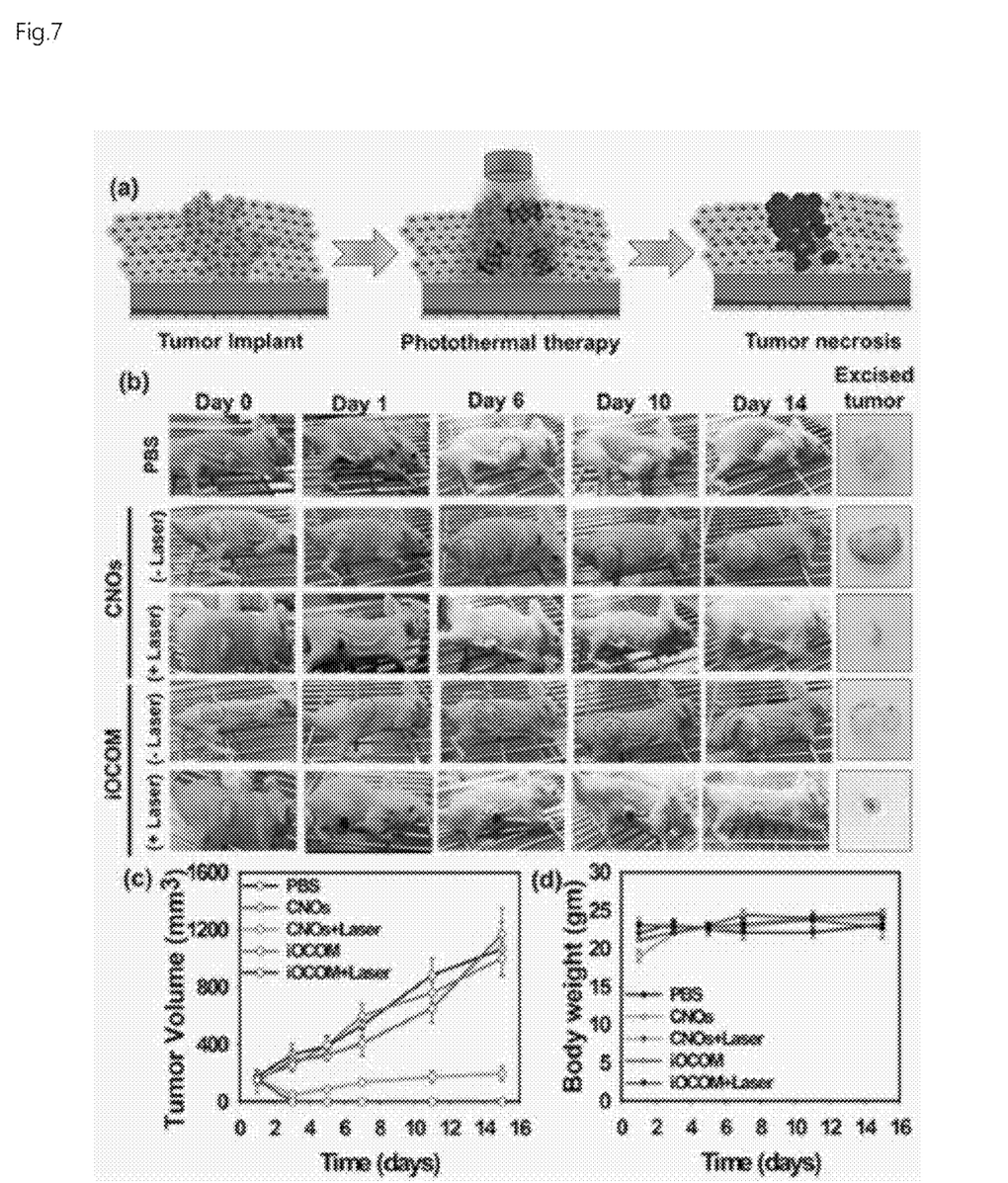
FIG. 7A is a schematic diagram for depicting PTT treatment.
FIG. 7B shows the monitoring results of tumor growth and corresponding ex-vivo tumor from Balb/c nude mice after PTT treatment.
FIGS. 7C and 7D show the measurement results of tumor volumes and body weights of the tumor-bearing mice, respectively.

Test Example 6—Measurement of Tumor Volumes and Body Weights after PTT Treatment Referring to FIG. 7A, after the PTT treatment, the tumor volumes and the body weights of the animals were monitored for 14 days. The iOCOMs (2 mg/kg) were administered in the KB tumor xenografts, and the tumors were irradiated with an NIR laser (2 W/cm$^2$) for 15 min. As shown in FIG. 7B, the animals treated with CNOs and iOCOMs without laser irradiation exhibited continuous tumor growth similar to that in the saline-treated animals. The animals treated with CNOs and laser irradiation exhibited reduced tumor growth compared with that in the control groups. Especially, referring to FIG. 7C, complete tumor ablation was observed in the animals treated with iOCOMs (2 mg/kg) with just a single dose of laser irradiation. In general, the high-power laser irradiation causes irreversible skin damage and immune activation, resulting in tumor recurrence after PTT. However, as shown in FIG. 7B, negligible traces of skin ablation as well as complete recovery of the skin to the normal condition were observed in the animals treated with iOCOMs. Referring to FIG. 7D, no significant changes in the animal body weights were observed in the laser-irradiated and non-irradiated animal groups. These results could confirm the efficacy of iOCOMs in PTT by preventing tumor relapse and causing negligible skin damage.

Figure 8:
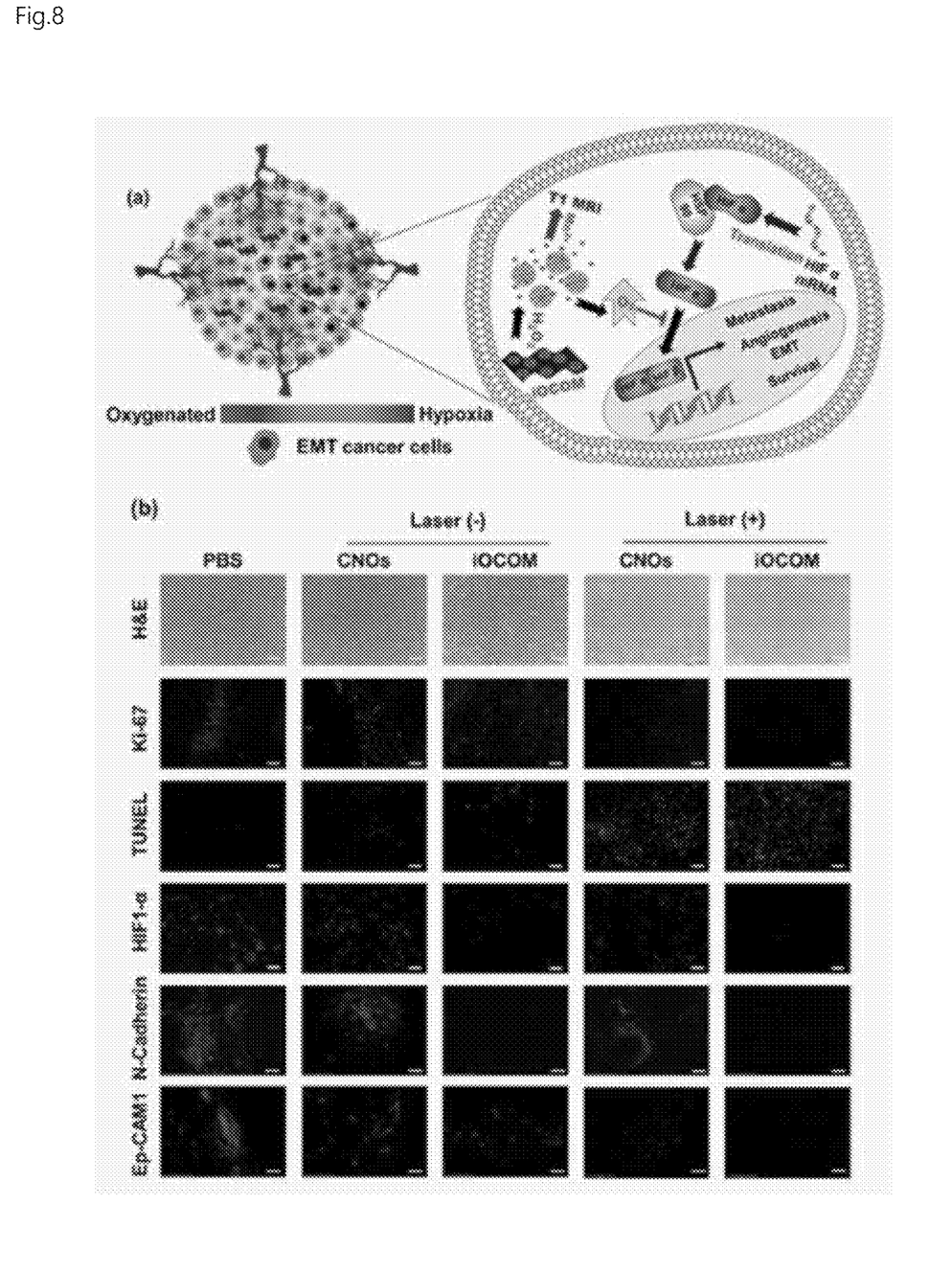
FIG. 8A is a schematic diagram for depicting the TME reprogramming by iOCOMs and effects thereof on molecular mechanisms in cancer cells.
FIG. 8B shows the histological analysis results of tumors after 14 days of PTT.

Test Example 7—TME Reprogramming by iOCOMs and Effects Thereof on Molecular Mechanisms in Cancer Cells Referring to FIG. 8A, hypoxia is known to be a potent regulator of several parameters in TME and plays an important role in tumorgenesis and the promotion of metastatic behaviors in cancer cells. Therefore, the effects of in-situ oxygenation-mediated hypoxia reprogramming by iOCOMs that modulate the molecular pathways of cancer cells were observed in the present test example. In the beginning, hematoxylin & eosin (H&E) staining of tumors was used to investigate the histological changes of the tumor tissue after PTT. As shown in FIG. 8B, the destruction of tumor cells, together with the disappearance of cell nuclei in the tumor tissue, was observed when tumor-bearing animals were treated with CNOs and iOCOMs under NIR laser irradiation. Moreover, excessive tissue damage and complete tumor necrosis were observed in the iOCOM-treated animals compared with those in the CNO-treated animals. Interestingly, the magnitude of tissue damage was significantly increased on day 15 compared with that on day 1 after PTT.

Since obvious pathological changes in the structures of the major primary organs (liver, spleen, lungs, kidneys, and heat) were not observed, the negligible toxicity and biocompatibility of iOCOMs were demonstrated.

The rate of cancer cell proliferation in the tumor tissues was studied using antigen Ki-67 assay. As shown in FIG. 8B, the animals treated with iOCOMs suppressed tumor cell proliferation compared with that in the other control groups.

In addition, the terminal deoxynucleotidyl transferase-mediated dUTP nick end labeling (TUNEL) assay was performed to study the level of tumor apoptosis after laser irradiation to the tumor tissues. As shown in FIG. 8B, enhanced green fluorescence (used as an apoptotic signal) was observed in the tumor sections treated with iOCOMs under laser irradiation.

The dismutation of $H_2O_2$ may result in the in situ production of dissolved oxygen in the TME, which can transmute the hypoxic cells to normoxia. Therefore, first, the expression of HIF1-α, a transcription factor responsible for the adaptation of cancer cells to a hypoxic TME, in the resected tumor tissues, was investigated. Interestingly, referring to FIG. 8B, the animals treated with iOCOMs with or without laser irradiation showed a marked reduction in HIF1-α expression in the tumor tissues. In normal physiological conditions, oxygen assists the hydroxyl group of proline residues (by prolyl hydroxylases, PHD) in HIF1-α, thereby inducing ubiquitination and reduced expression in cells. However, the hypoxic TME assists in the ubiquitination of PHD and stimulates the expression of HIF1-α in cancer cells. The reduction of $H_2O_2$ together with increased oxygen levels during the dismutation of iOCOMs can accelerate the HIF1-α degradation in cancer tissue, thereby preventing the ubiquitination of PHDs.

During the initiation of cancer metastasis, cancer cells alter the expression of cell-adhesion molecules (such as, cadherins) to result in the detachment from primary tumors. N-cadherin is one of the transmembrane proteins that are highly expressed in the metastatic cancer cells that can favor the migration and motility of cancer cells, and is regarded as a hallmark for cancer metastasis. By activating the expression of N-cadherin in cancer cells, the hypoxic environments and the activation of HIF1-α signaling pathways can stimulate the metastasis of cancer cells. As shown in FIG. 8B, the increased secretion of N-cadherin was observed in control or CNO-treated tumors. However, the rapid tumor oxygenation by iOCOMs in the hypoxic TME reduced the expression of HIF1-α in the cancer cells, which further down-regulated the N-cadherin expression in both laser- and non-laser-treated animals.

The ectopic expression of epithelial cell-adhesion molecules (Ep-CAM1) is associated with the epithelial to mesenchymal transition (EMT) and the induction of stem-cell-like phenotype characteristics in cancer tissues. A significant reduction in Ep-CAM1 expression was observed in the tumor sections of iOCOM-treated animals in the presence or absence of laser irradiation. These results show that the rapid in situ oxygenation by iOCOMs can reprogram the TME and produce main effects on the physiological behavior of cancer cells.

The features, structures, effects, and the like described in the above embodiments are included in at least one embodiment of the present disclosure and are not necessarily limited to one embodiment. Furthermore, the features, structures, effects, and the like illustrated in each embodiment may be combined or modified into other embodiments by those skilled in the art to which the embodiments pertain. Accordingly, the contents related to such combination or modification should be interpreted as being included in the scope of the disclosure.

The present disclosure has been described mainly with reference to embodiments, but these embodiments are merely exemplified and do not limit the present disclosure. It will be understood by those skilled in the art that various modifications and applications, not illustrated above, may be made without departing from the substantial features of the present disclosure. For example, respective elements specifically shown in the embodiments can be modified and implemented. It should be interpreted that differences related to such modifications and applications are included in the scope of the present disclosure defined in the appended claims.

What is claimed is:

1. A method of treating a tumor,
the method comprising administering an effective amount of a nanocomplex,
wherein the nanocomplex comprises a manganese dioxide ($MnO_2$) sheet; and
carbon nano-onions (CNOs) embedded in the manganese dioxide sheet,
wherein CNOs have 7 to 8 onion rings,
wherein the interplanar d lattice spacing of the CNOs is 0.34 nm.

2. The method of claim 1, wherein the carbon nano-onions are synthesized through pyrolysis of deoxycholic acid (DOCA).

3. The method of claim 1, wherein the nanocomplex is synthesized by reducing potassium permanganate ($KMnO_4$) to $MnO_2$ in the presence of the carbon nano-onions.

* * * * *